(12) United States Patent
Freyman et al.

(10) Patent No.: US 7,396,351 B2
(45) Date of Patent: Jul. 8, 2008

(54) DEVICE AND METHOD FOR THE DELIVERY OF VISCOUS FLUIDS IN THE BODY

(75) Inventors: Toby Freyman, Watertown, MA (US); Maria Palasis, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 611 days.

(21) Appl. No.: 10/700,569

(22) Filed: Nov. 5, 2003

(65) Prior Publication Data

US 2005/0096636 A1    May 5, 2005

(51) Int. Cl.
*A61M 25/18*    (2006.01)

(52) U.S. Cl. .................................................. 604/537

(58) Field of Classification Search ................ 604/537, 604/245–247, 73–75, 266–267, 523, 256, 604/101.01, 6.1, 6.11, 6.9; 623/1.3
See application file for complete search history.

(56) References Cited

U.S. PATENT DOCUMENTS

| | | | |
|---|---|---|---|
| 4,690,673 A | 9/1987 | Bloomquist | |
| 4,781,678 A * | 11/1988 | de Couet et al. | 604/45 |
| 5,163,910 A | 11/1992 | Schwartz et al. | |
| 5,222,980 A * | 6/1993 | Gealow | 623/3.12 |
| 5,320,605 A * | 6/1994 | Sahota | 604/101.01 |
| 5,620,313 A * | 4/1997 | Fockenberg | 417/475 |
| 5,861,010 A | 1/1999 | Boussignac et al. | |
| 6,004,288 A * | 12/1999 | Hochstedler et al. | 604/74 |
| 6,053,899 A | 4/2000 | Slanda et al. | |
| 6,056,743 A | 5/2000 | Ellis et al. | |
| 6,238,406 B1 | 5/2001 | Ellis et al. | |
| 6,416,490 B1 | 7/2002 | Ellis et al. | |
| 2003/0094736 A1 * | 5/2003 | Qin et al. | 264/485 |

FOREIGN PATENT DOCUMENTS

| | | |
|---|---|---|
| WO | WO 00/67646 A1 | 11/2000 |
| WO | WO 00/67647 A1 | 11/2000 |
| WO | WO 01/41657 A1 | 6/2001 |
| WO | WO 02/49695 A2 | 6/2002 |
| WO | WO 03/015841 A2 | 2/2003 |

OTHER PUBLICATIONS

International Search Report for PCT Application No. US2004/034505, filed Oct. 20, 2004, 5 pages.

* cited by examiner

*Primary Examiner*—Nicholas D. Lucchesi
*Assistant Examiner*—Theodore J Stigell

(57) ABSTRACT

An apparatus and method for delivering a viscous liquid therapeutic material fluid through a lumen in a catheter that selectively narrows the lumen at a plurality of axial locations along the lumen.

9 Claims, 5 Drawing Sheets

DEVICE AND METHOD FOR THE DELIVERY OF VISCOUS FLUIDS IN THE BODY

BACKGROUND OF THE INVENTION

This invention relates generally to catheters, and more particularly, to a catheter for delivering a viscous therapeutic material.

There are many instances in which it is desirable to deliver a therapeutic material to a target location, such as directly to tissue to be treated by the therapeutic material. Relatively low viscosity fluids (comprising or carrying therapeutic material) may be readily delivered with conventional catheters in minimally invasive procedures. However, low viscosity fluids are often retained poorly following injection into tissues, particularly in tissues such as the myocardium. Although relatively high viscosity fluids may have higher retention, and some therapeutic materials are only available in high viscosity forms, they may be difficult or impossible to deliver at acceptable flow rates with acceptable delivery pressures through the long, narrow catheters typically used for minimally invasive procedures.

SUMMARY OF EMBODIMENTS OF THE INVENTION

The disclosed embodiments of methods and apparatuses strive to address some of the disadvantages and limitations of known techniques for delivering viscous therapeutic materials. These embodiments employ various techniques for selectively narrowing a lumen through which the viscous materials can be transported.

DETAILED DESCRIPTION OF THE INVENTION

Figure 1A:
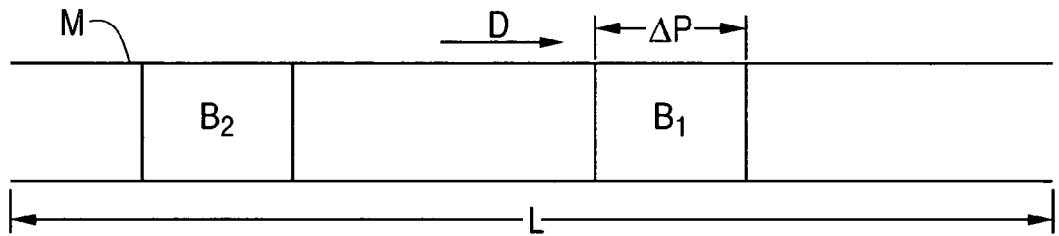
FIGS. 1A and 1B are schematic illustrations of the movement of a bolus of viscous therapeutic material through a catheter lumen in accordance with the principles of the invention.

The various embodiments of apparatuses and methods disclosed below are for the delivery of one or more therapeutic materials in a fluid, more specifically, in a high viscosity fluid. The therapeutic material can be delivered to any desired location, typically internal to a human or other body. In one embodiment, the therapeutic material is delivered into a body cavity or deposited or inserted into an organ or other tissue. One exemplary application is delivery or implantation of therapeutic material into the myocardium.

As used herein, the terms "therapeutic agent," "therapeutic material," "active material," and similar terms includes, but is not limited to, any therapeutic agent or active material, such as drugs, genetic materials, and biological materials. Suitable genetic materials include, but are not limited to, DNA or RNA, such as, without limitation, DNA/RNA encoding a useful protein and DNA/RNA intended to be inserted into a human body including viral vectors and non-viral vectors. Suitable viral vectors include, for example, adenoviruses, gutted adenoviruses, adeno-associated viruses, retroviruses, alpha viruses (Semliki Forest, Sindbis, etc.), lentiviruses, herpes simplex viruses, ex vivo modified cells (e.g., stem cells, fibroblasts, myoblasts, satellite cells, pericytes, cardiomyocytes, skeletal myocytes, macrophage), replication competent viruses (e.g., ONYX-015), and hybrid vectors. Suitable non-viral vectors include, for example, artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

Suitable biological materials include, but are not limited to, cells, yeasts, bacteria, proteins, peptides, cytokines, hormones, matrices (such as extracellular matrices), and natural polymers (such as hyaluronic acid). Examples of suitable peptides and proteins include growth factors (e.g., FGF, FGF-1, FGF-2, VEGF, Endotherial Mitogenic Growth Factors, and epidermal growth factors, transforming growth factor α and β, platelet derived endothelial growth factor, platelet derived growth factor, stem cell factor, tumor necrosis factor α, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, and BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at a desired site. The delivery media can be formulated as needed to maintain cell function and viability. For example, the delivery media may include polymers or protein carriers for therapeutics so that the polymer increases viscosity and retention of the therapeutic material and may increase cell survival once delivered to the tissue. Cells include, for example, whole bone marrow, bone marrow derived mono-nuclear cells (BM-MNC), progenitor cells (e.g., endothelial progenitor cells (EPC)), stem cells (e.g., mesenchymal (MSC, including MSC+5-aza), hematopoietic, neuronal, cardiac, or other tissue derived, embryonic stem cells and stem cell clones), pluripotent stem cells, fibroblasts, MyoD scar fibroplasts, macrophage, side populations (SP) cells, lineage negative (Lin−) cells (including Lin−CD34−, Lin−CD34+, and Lin−cKit+)), cord blood blood cells, skeletal myoblasts, muscle-derived cells (MDC), Go cells, endothelial cells, adult myocardiomyocytes, smooth muscle cells, adult cardiac fibroplasts +5-aza, pacing cells, fetal or neonatal cells, immunologically masked cells, genetically modified cells, teratoma derived cells, and satellite cells, and tissue engineered grafts.

The term "therapeutic agent" and similar terms also includes non-genetic agents, such as: anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, antithrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides; vascular cell growth promotors such as growth factors, Vascular Endothelial Growth Factors (VEGF, all types including VEGF-2), growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents, vasodilating agents, and agents which interfere with endogenous vasoactive mechanisms; anti-oxidants, such as probucol; antibiotic agents, such as penicillin, cefoxitin, oxacillin, tobranycin; angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

Preferred therapeutic materials include angiogenic genes or proteins and stem cells. Other suitable therapeutic materials may include anti-proliferative drugs such as steroids, vitamins, and restenosis-inhibiting agents such as cladribine. Restenosis-inhibiting agents include microtubule stabilizing agents such as Taxol, paclitaxel, paclitaxel analogues, derivatives, and mixtures thereof. For example, derivatives suitable for use in the invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt. Other suitable therapeutic materials include nitroglycerin, nitrous oxides, antibiotics, aspirins, digitalis, and glycosides.

As described above, the invention relates to the delivery of high viscosity therapeutic material. A goal is to deliver a desired volume of the therapeutic material within an acceptable time at an acceptably low pressure through a catheter that is long enough to reach the desired location for discharge of the therapeutic material and that has a diameter or width that is acceptably small. If the therapeutic material fills and continuous lumen of the catheter and is simply forced through the lumen by creating a pressure differential between the proximal and distal ends of the lumen, then the relationship among these various parameters can be examined by analyzing the flow of the therapeutic material as fully developed laminar flow in a pipe. Thus, the flow Q is calculated as:

$$Q = \frac{\Delta P}{R}$$

where $\Delta P$ is the pressure differential and R is calculated by:

$$R = \frac{8\eta L}{\pi r^4}$$

where $\eta$ is the dynamic viscosity of the therapeutic material, L is the length of the lumen, and r is the radius of the lumen.

Thus, for a given desired flow rate, the required pressure differential scales linearly with viscosity, inversely with length, and inversely with the fourth power of the radius of the lumen. Given the desire to deliver a particular therapeutic agent (i.e. of a predetermined, high viscosity) at an acceptable flow rate, through a catheter of acceptably small radius and of the length required (dictated by the physiology of the subject and the minimally invasive technique) the required pressure differential can be unacceptably high.

The approach taken in the disclosed invention is to reduce the length over which shear forces within the therapeutic material (and between the material and the inner wall of the delivery lumen) can act and across which the pressure differential must be established. This therefore reduces the magnitude of the required pressure differential. As illustrated schematically in FIG. 1A, this can be viewed as moving one or more boluses $B_1$, $B_2$ of therapeutic material through a lumen M having a length L (rather than a continuous flow), with a pressure differential $\Delta P$ established across an individual bolus to move the bolus through lumen M.

The pressure differential $\Delta P$ across a bolus required to urge the bolus through lumen M could be created in many ways. In the disclosed invention, the pressure differential is created by narrowing the lumen on the proximal side of the bolus while maintaining, or opening, the lumen on the distal side of the bolus.

The term "narrowing" is used to mean a reduction in the cross-sectional area of the lumen available to be occupied by the therapeutic material. The narrowing can be accomplished by constricting, flattening, or otherwise deforming the lumen to reduce its cross-sectional area. Alternatively, or additionally, it can be accomplished by introducing into the interior of the lumen some object or material that occupies some of the cross-sectional area otherwise available to the therapeutic material. The narrowing produces a force, and therefore a pressure, on the proximal portion of the bolus that exceeds the pressure on the distal side, therefore urging the bolus distally through the lumen.

The narrowing and opening of the portions of the lumen adjacent the bolus is preferably conducted sequentially and repeatedly, in a manner similar to peristaltic motion of a natural lumen (such as the esophagus) so that the bolus is urged along the length of the lumen by a series of sequential narrowings of the lumen, proximally to distally. The narrowings (and openings) may be a series of discrete narrowings (and openings), or may be continuous, as described below in more detail.

Figure 1B:
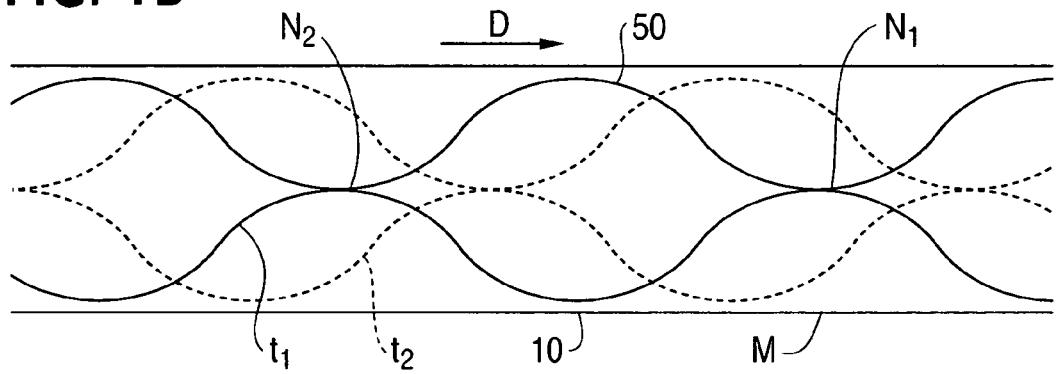

This "peristaltic" motion is illustrated schematically in FIG. 1B. A catheter 10 includes a rigid exterior wall 30 defining a main lumen, and an inner, fluid transporting lumen M defined by a deformable lumen wall 50. A bolus $B_1$ of viscous fluid travels distally (in the direction indicated by arrow D) through lumen M by the distal translation of narrowings $N_1$ and $N_2$ on the distal and proximal sides, respectively, of bolus $B_1$. Note that as illustrated in FIG. 1B, the narrowings are achieved by a constrictive deformation of the lumen wall 50. The distal translation is seen by comparing the locations of the narrowings $N_1$ and $N_2$ at a time $t_1$ (at which time the disposition of lumen wall 50 is shown in solid lines) and a subsequent time $t_2$ (at which time the disposition of lumen wall 50 is shown in dashed lines).

Figure 2A:
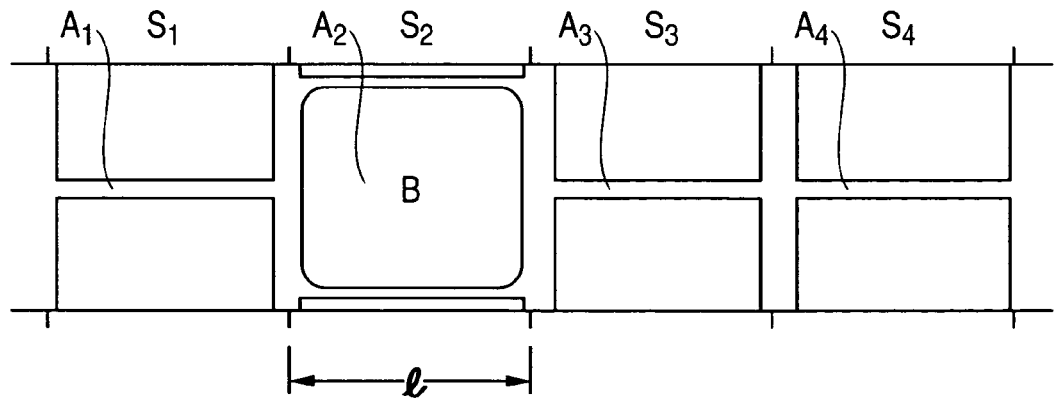
FIGS. 2A through 2C are schematic illustrations of the motion of a bolus of therapeutic material through a catheter lumen in accordance with the principles of the invention.
Figure 2B:
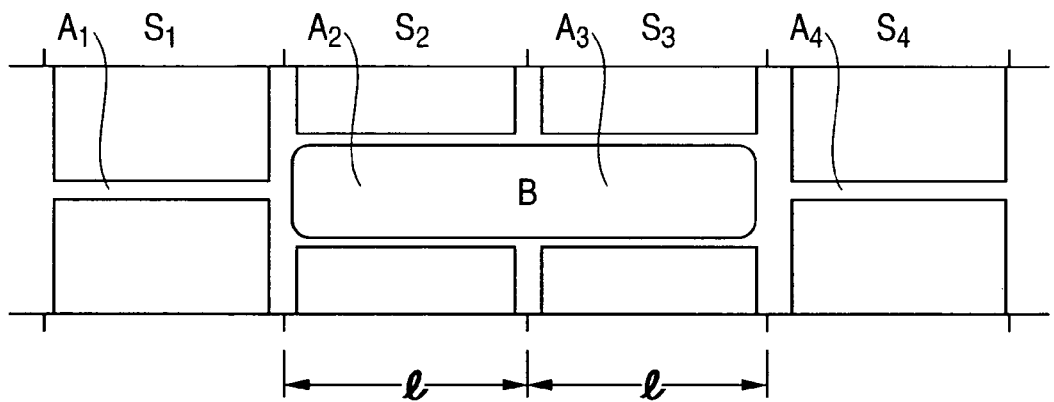
Figure 2C:
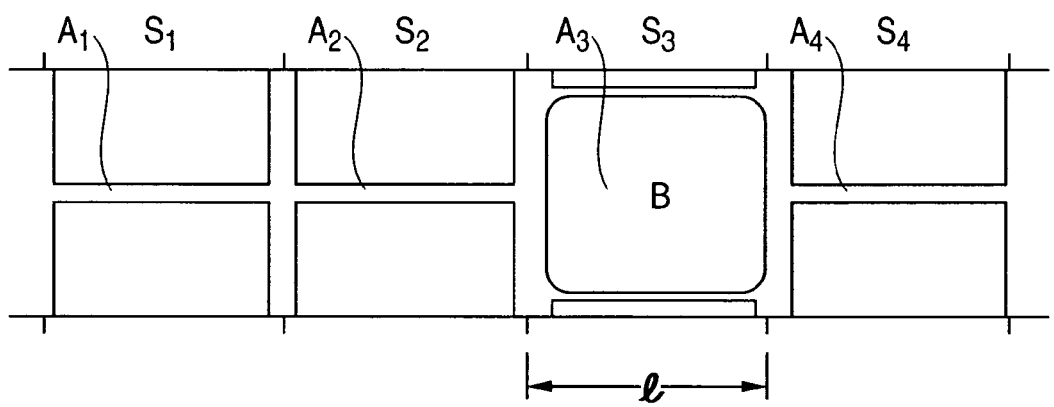

FIGS. 2A-2C further illustrate schematically the distal motion of a bolus B1 through a delivery lumen M. A section of lumen M can be divided conceptually into a series of axial segments $S_1$, $S_2$, $S_3$, $S_4$, etc., each having the same length, l. Each segment also has an average cross-sectional area $A_1$, $A_2$, $A_3$, $A_4$, etc. available to contain a portion of bolus $B_1$.

Thus, each segment $S_i$ has an available volume $V_i$ defined by $V_i = l \times A_i$. Bolus $B_1$ has a volume $V_b$ (which is assumed to be constant, since the bolus consists of incompressible liquid), which in the illustrated example is equal to the maximum volume of each segment S. Bolus $B_1$ can therefore occupy a single segment at its maximum volume, or span multiple segments when the segments are narrowed from their maximum area A. Thus, in the illustrated example, bolus $B_1$ initially occupies segment $S_2$ (as shown in FIG. 2A).

To move bolus $B_1$ distally, segment $S_2$ is narrowed and segment $S_3$ is opened, thus urging a portion of bolus $B_1$ from segment $S_2$ to segment $S_3$ (as shown in FIG. 2B,. Bolus $B_1$ is moved further distally by further narrowing segment $S_2$ and opening segment $S_3$ to its maximum area, so that bolus $B_1$ occupies only segment $S_3$ (as shown in FIG. 2C). This sequence could be repeated with segments $S_3$ and $S_4$ to move bolus $B_1$ from segment $S_3$ to segment $S_4$.

In the process as described above, it is assumed that when segment $S_i$ is narrowed, the bolus is displaced into segment $S_{i+1}$, and not into segment $S_{i-1}$. As illustrated schematically in FIGS. 2A-2C, the segments not containing all or part of bolus $B_1$ are shown at a minimum cross sectional area providing little or no area through which (or volume into which) bolus $B_1$ can flow. Conceptually, segment $S_{i-1}$ can be considered as a valve if it is narrowed to a sufficiently small (or zero) cross-sectional area.

As explained in more detail below in connection with some of the disclosed embodiments, a mechanical valve can be employed to inhibit or prevent undesired flow in the proximal direction, and the opening or closing of the valve(s) can be coordinated with the narrowing and opening of the delivery lumen in adjacent segments. In the several embodiments illustrated in FIGS. 3 to 10 below, the delivery lumen is literally divided into a series of segments or chambers, each separated from the others by a selectively openable and closable partition or valve.

Figure 3A:
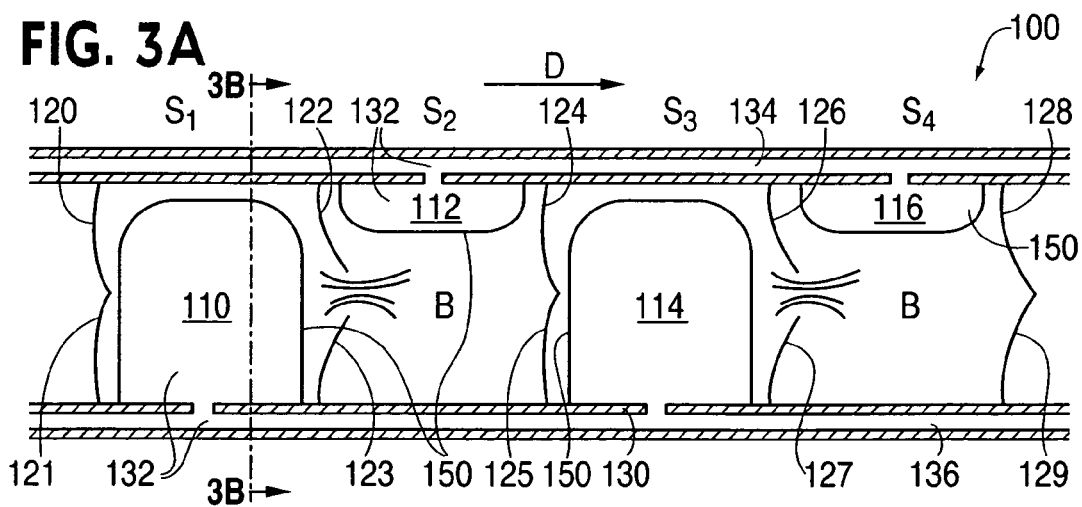
FIG. 3A is a schematic illustration of a catheter for delivering therapeutic material in a high viscosity fluid in accordance with one embodiment of the invention.
Figure 3B:
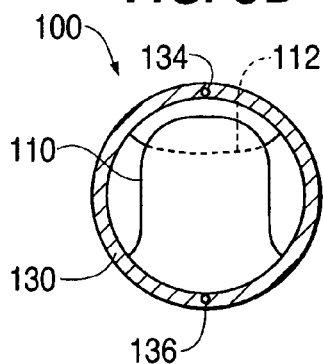
FIG. 3B is a cross-sectional schematic illustration of the catheter of FIG. 3 taken along line 3B-3B.

A first embodiment of a catheter 100 is illustrated schematically in FIGS. 3A and 3B. Catheter 100 has a body B containing a delivery lumen M defined by relatively rigid lumen walls 130. Delivery lumen M is divided into a series of chambers or segments $S_1$, $S_2$, $S_3$, $S_4$ by a series of partitions 120, 122, 124, 126, 128. Each partition includes a valve (which in the illustrated embodiment is a check valve, such as a conventional "duck-bill" valve) 121, 123, 125, 127, 129, respectively. Each valve opens, and allows the liquid therapeutic material to pass through distally, in response to establishment of a predetermined pressure differential across the valve, with the pressure on the proximal side higher than the pressure on the distal side. Delivery lumen M is selectively narrowed within each segment S by displacing volume available to the therapeutic material.

In the illustrated embodiment, this is accomplished with a selectively collapsible and extendable member or balloon 110, 112, 114, 116 disposed in segments $S_1$, $S_2$, $S_3$, $S_4$, respectively. Each of the balloons is formed of a closed elastic membrane 150 into which a pressurized drive fluid 132 can be introduced or withdrawn to inflate or deflate, respectively, the balloon. The balloon may be formed of any suitable material, such as nylon, polyethylene terephthalate ("PET"), or silicone. The drive fluid 132 can be a gas that is soluble in the blood (e.g. $CO_2$) or, more preferably, a liquid such as saline or any other suitable fluid. When the amount of drive fluid 132 within a balloon is increased, the balloon expands away from wall 130 by stretching the elastic covering 150 of the balloon. In the illustrated embodiment, each balloon can expand until it substantially fills the segment S in which it is located. When all of the drive fluid 132 is withdrawn from a balloon, the balloon retracts until it is substantially flat against the lumen wall 130.

FIG. 3B shows member 110 in an expanded state and member 112 in a collapsed state. When member 110 is extended or expanded, it narrows lumen 100. When member 112 is collapsed, it is substantially adjacent to rigid wall 130 of lumen M.

Drive fluid 132 is supplied to the balloons via manifolds or supply lines 134, 136. In the illustrated embodiment, alternating balloons 110, 114 are fluidically coupled to supply line 136, while balloons 112, 116 are fluidically coupled to supply line 134. This allows one set of alternating balloons to be simultaneously expanded by supplying additional, higher-pressure drive fluid through supply line 136 and the other alternating set of balloons to be simultaneously collapsed by withdrawing (or allowing to be expelled) drive fluid 132 from supply line 134.

Catheter 100 is operated as follows to delivery a bolus of therapeutic material $B_1$ initially disposed in segment $S_1$. Initially, balloons 110 and 114 are in their collapsed positions, while balloons 112 and 116 are in their expanded positions. The pressure of drive fluid 132 is increased in supply line 136 (and thus in balloons 110 and 114), while the pressure of drive fluid 132 is reduced in supply line 134 (and thus in balloons 112 and 116). The increased pressure in balloon 110 is transmitted to bolus B disposed in segment $S_1$. Similarly, the reduction in the pressure in balloon 112 reduces the pressure of any fluid in segment $S_2$. When the pressure differential across valve 123 (between segments $S_1$ and $S_2$) exceeds the opening pressure differential of valve 123, the valve opens. Drive fluid is introduced at the same or greater pressure into supply line 136, and is withdrawn or expelled from supply line 134, thus expanding balloon 110 and reducing or collapsing balloon 112. In turn, this causes bolus $B_1$ to flow through valve from segment $S_1$ into segment $S_2$. When balloon 110 is fully extended or expanded, and balloon 112 is fully collapsed, bolus $B_1$ occupies segment $S_2$.

Another cycle can then be performed, in which the pressure of drive fluid 132 in supply line 134 is increased, and the pressure of drive fluid 132 in supply line 136 is reduced. This leads to increased pressure in balloon 112 (and segment $S_2$) and reduced pressure in balloon 114 (and segment $S_3$). Valve 125 opens when the requisite pressure differential between segments $S_2$ and $S_3$ is achieved, and bolus $B_1$ is displaced distally by expanding balloon 112 from segment $S_2$ to $S_3$ through valve 125.

While there are various mechanisms for supplying the drive fluid for extending and collapsing the members 110, the method exemplified schematically in FIGS. 3A, 3B shows two fluid supply lines or plenums 134, 136 to convey drive fluid 132.

It is contemplated, and the artisan will recognize, that many techniques would be suitable for supplying, and controlling the flow of, drive fluid 132 to members or balloons 110, 112, 114, 116. There could be a single supply plenum and a single return plenum, with each balloon coupled by suitable valves to both plenums. The balloons could be expanded by opening the valve to the supply plenum and closing the valve to the return plenum, and could be contracted by reversing the settings of the valves. Alternatively, each balloon (or sets of alternate balloons), could be coupled to a dedicated plenum through which fluid can be introduced into, and withdrawn from, the balloon.

Valves 121, 123, 125, 127, 129 are illustrated as "duckbill" check valves. Any other suitable check valve (such as a ball valve) that opens in response to a predetermined pressure differential, could be used. Alternatively, each valve could be opened and closed independently of the pressure across the valve using a suitable valve structure, actuator, and control.

FIGS. 4A to 5B schematically illustrate two alternative catheters similar in structure and operation to the catheter illustrated in FIGS. 3A and 3B. These alternative embodiments include alternative shapes and configurations for the collapsible and expandable members 210.

Figure 4A:
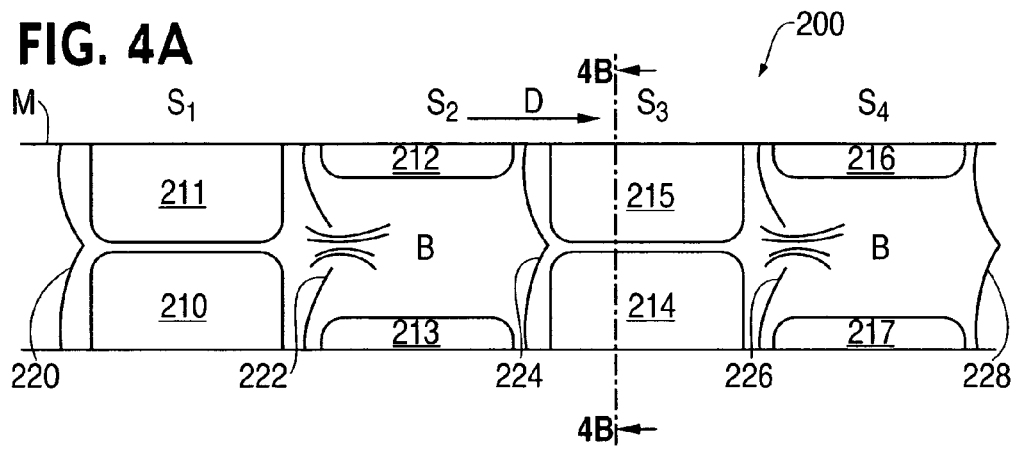
FIG. 4A is a schematic illustration of an alternative embodiment of the catheter of FIG. 3A.
Figure 4B:
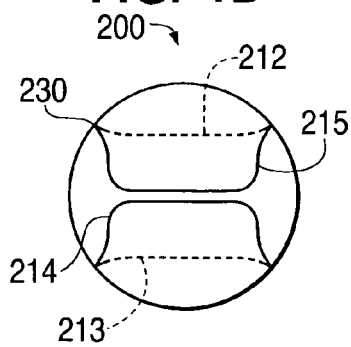
FIG. 4B is a cross-sectional schematic illustration of the catheter of FIG. 4A, taken along line 4B-4B.

The catheter illustrated in FIGS. 4A and 4B includes additional members 211, 213, 215, 217 disposed on opposing sides of the delivery lumen M. Opposing members 210-211, 212-213, 214-215, 216-217 meet (or come close to each other) in the center the lumen M when expanded to narrow the lumen M with two members instead of the single member shown in FIGS. 3A and 3B. Each pair of members 210-211, 212-213, 214-215, 216-217 in the same segment $S_i$ expands or contracts in unison to create a change in the area inside of the lumen M at the segment $S_i$. The operation of the alternating expanded and contracted pairs of members 210-217 is the same as discussed above with reference to FIGS. 3A and 3B, creating a pressure differential operative to move a bolus B distally (in the direction indicated by arrow D) through the valves 220, 222, 224, 226.

Figure 5A:
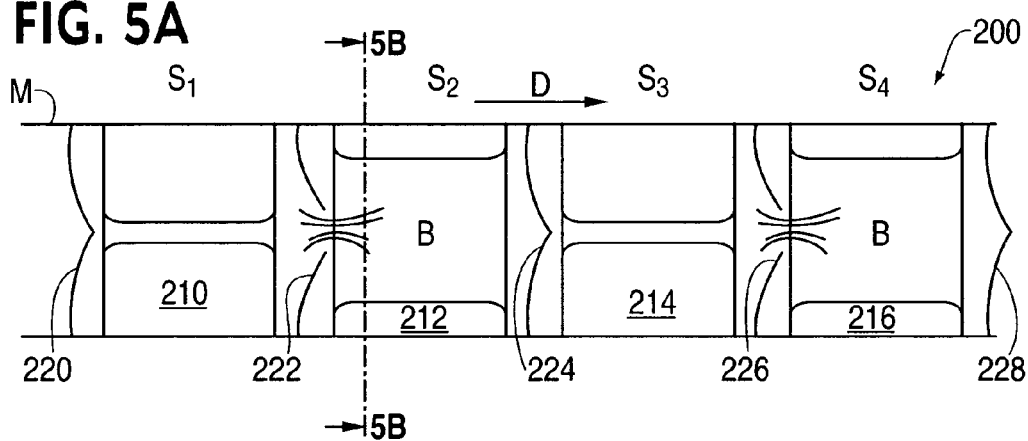
FIG. 5A is a schematic illustration of another alternative embodiment of the catheter of FIG. 3A.
Figure 5B:
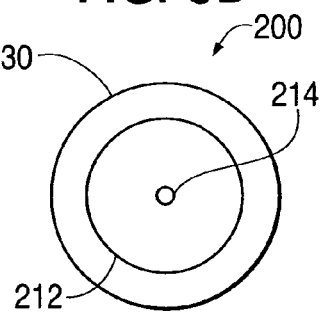
FIG. 5B is a cross-sectional schematic illustration of the catheter of FIG. 5A, taken along line 5B-5B.

In the alternative embodiment illustrated in FIGS. 5A and 5B, the collapsible and expandable members 210, 212, 214, 216 are annular or toroidal. Each of the members 210, 212, 214, 216 is attached to the wall 230 of the lumen M in a ring on the inner surface in its respective segment $S_i$. As the members 210, 212, 214, 216 expand, the ring narrows and the center of the ring collapses, creating a substantially narrowed portion of the lumen M. The operation of the alternating expanded and contracted members 210, 212, 214, 216 is the same as discussed above with reference to FIGS. 3A and 3B, creating a pressure differential operative to move the bolus distally (in the direction indicated by arrow D) as described above through the valves 220, 222, 224, 226, 228.

Figure 6:
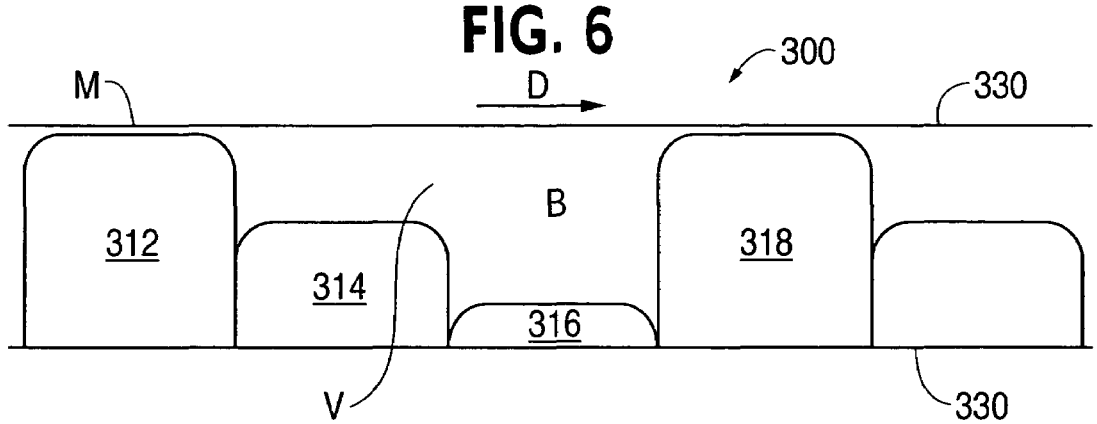
FIGS. 6-10 are schematic illustrations of other embodiments of catheters for delivering therapeutic material in a high viscosity fluid.

Another alternative embodiment of a catheter is illustrated schematically in FIG. 6. In this embodiment, the function of the partitions and valves of catheter 200 is performed instead by additional balloons. Catheter 300 includes elastic, collapsible and expandable members or balloons 312, 314, 316, 318 located in lumen M.

Each of the balloons is selectively collapsible or extendable by modifying the volume of the balloons through the addition or removal of drive fluid via suitable means, such as described above in connection with FIGS. 3A and 3B. However, in this embodiment, rather than having every other balloon expand and contract in unison, every third balloon operates in unison, as described in more detail below. Thus, one approach to supplying drive fluid would be to have three supply lines or manifolds, with every third balloon fluidically coupled to one of the lines.

As illustrated, when one balloon or member 314 is expanded, the adjacent member 316 is collapsed, while another member 312 is maintained in a fully expanded state. Member 31 thus serves to inhibit or reduce displacement of liquid in bolus B in the proximal direction (opposite to the distal direction indicated by arrow D). Member 31 thus functions similar to the check valve described in the prior embodiments. The three members 312, 314, 316 are expanded and contracted in sequence in a manner similar to that described above with reference to FIGS. 2A-2C. Thus a fluid conveying volume V (as shown, containing bolus B) is urged or displaced distally along the length of the catheter by lessening the volume in one segment and increasing the volume in the adjacent, distally subsequent section of lumen M, creating a pressure differential to push bolus B distally along lumen M.

Once member 314 is fully expanded, member 318 begins to collapse, and intervening member 316 begins to expand. The process described above is repeated and the bolus B is further pushed distally along lumen M.

Note that lumen 300 has a wall 330 that is sufficiently rigid that it is not distended by pressure in the balloons.

While the illustrated embodiment is shown to function with the interaction of three members, a selective expanding and contracting of a larger number of members could create a similar movement as long as the collective fluid conveying volume V defined by the balloons within the segments of the lumen is maintained by expanding the balloons on the proximal side of the volume V and collapsing the balloons on the distal side, thus creating the difference in pressure required to push the bolus B in the distal direction D with a peristaltic motion. Thus, the sequencing of the expansion and collapse of the balloons could be done with sets of four, five, or more balloons.

Figure 7:
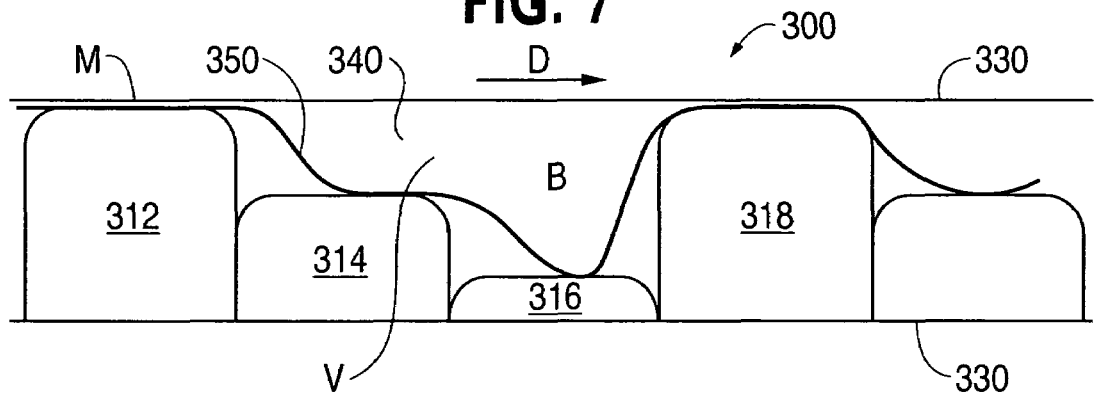

A further alternative embodiment is illustrated in FIG. 7. Catheter 300 in this embodiment is similar to that shown in FIG. 6, except that it includes an inner, fluid transport lumen 340 as defined in part by the external wall 330 and in part by an elastic lumen wall 350. The inner lumen 340 transports the bolus B. Catheter 300 operates similarly to that illustrated in FIG. 6, with the balloons or members 312, 314, 316, 318 selectively collapsing and extending to create a peristaltic motion moving the fluid conveying volume V (containing bolus B) contained in the inner lumen 340 in the distal direction D. Rather than being defined partly by external wall 330, inner lumen 340 could be defined only by a tubular elastic wall.

Figure 8:
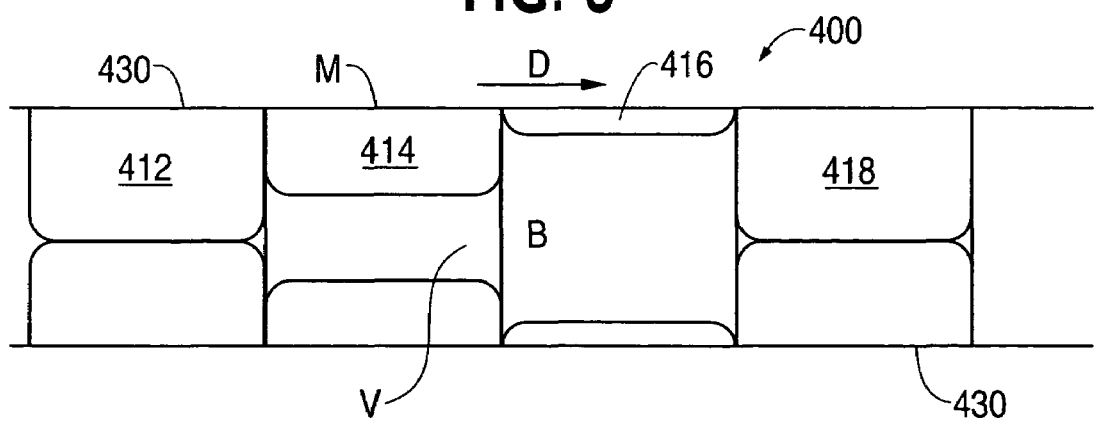

In a further alternative embodiment, illustrated schematically in FIG. 8, a catheter 400 includes several annular or toroidal elastic, collapsible and extendable members or balloons. Members 412, 414, 416, 418 is similar to members 210, 212, 214, 216 as illustrated in FIGS. 5A and 5B and discussed above. The operation of catheter 400 is similar to that of catheter 300 as illustrated in FIGS. 6 and 7—members 412, 414, 416 and 418 are selectively collapsed and expanded to create a peristaltic motion to displace fluid conveying volume V distally.

As with the embodiments of FIGS. 6 and 7, an inner, elastic fluid transport can be placed in the catheter 400, within lumen M, to be constricted externally by members 412, 414, 416, 418, which would be selectively expanded and collapsed in the same motion to exert pressure on the inner lumen and create a peristaltic motion to push a bolus of fluid along the length of the catheter 400.

In the embodiments described above, a fluid-based drive is employed to move a fluid conveying volume (and urge a fluid bolus) along the lumen of the catheter. Thus, hydraulic or pneumatic systems are used to expand and contract elastic balloons and thus to selectively narrow the fluid transport lumen by constricting or occluding it. An alternative approach relies on movement of a rigid displacement member, rather than expansion and contraction of an elastic balloon.

Figure 9:
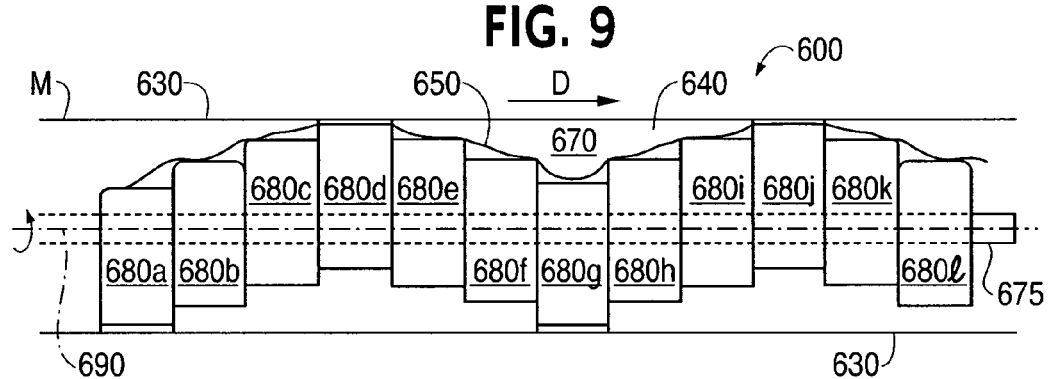

One embodiment of a catheter employing this approach is illustrated schematically in FIG. 9. The illustrated catheter 600 includes a lumen M with a rigid wall 630 and an inner lumen 640 defined by the rigid wall 630 and a flexible, pliable inner lumen wall 650. The catheter also includes a cam system 670, with a shaft 675 mounted for rotation about an axis 690 and supporting cams 680.

Cams 680 are disposed to selectively constrict lumen 640. Each cam 680 is shaped such that in one revolution of the cam shaft 675 around axis 690, the cam 680 narrows (constricts) inner lumen 640 for part of the rotation, and allows the inner lumen 640 to expand over part of the rotation. Preferably, when narrowing the inner lumen 640, each cam member 680 presses the pliable inner lumen wall against the rigid outer wall 630 to inhibit the flow of fluid in the proximal direction.

In the illustrated embodiment, as shaft 675 rotates about axis 690, cams 680*d* and 680*j* are fully narrowing the inner lumen 640 and other cams 680*a*, 680*g* are the maximum distance from the rigid wall 630 on the side of the inner lumen 640, allowing the maximum volume in the inner lumen at the section of the catheter occupied by the cams 680*a*, 680*g*. As shaft 675 turns, cams 680*h*, 680*i*, and 680*j* allow expansion of the inner lumen on the distal end of bolus B, and cams 680*e*, 680*f*, and 680*g* begin to constrict the inner lumen 640 on the proximal side of bolus B. This motion of constriction and expansion pushes bolus B along lumen M in the distal direction D, in a peristaltic motion similar to that discussed above for the other embodiments.

The eccentrically mounted cam members in this embodiment function as rigid displacement members to selectively narrow the fluid transport lumen. Numerous alternative implementations of such displacement members are envisioned, and would be apparent to the artisan. For example, the cam system could be replaced with a series of pistons arrayed along the length of the lumen and disposed for reciprocal motion toward and away from the deformable lumen. Such pistons could be driven mechanically, magnetically (e.g. a solenoid), or otherwise.

In the embodiments described above, the lumen is narrowed by radial movement of a displacement member (either an expandable balloon or a rigid structure such as a cam) at a fixed axial location in the catheter (or with respect to the lumen). The fluid conveying volume (containing a fluid bolus) is defined between two adjacent narrowed portions of the lumen. This volume is translated distally by the successive narrowing of displacement members distally adjacent to the members previously defining the ends of the volume. The motion of the volume is thus discrete or incremental. In an alternative approach, the locations at which the lumen is narrowed are moved continually along the lumen. This approach is described in connection with the embodiment illustrated schematically in FIG. 10.

Figure 10:
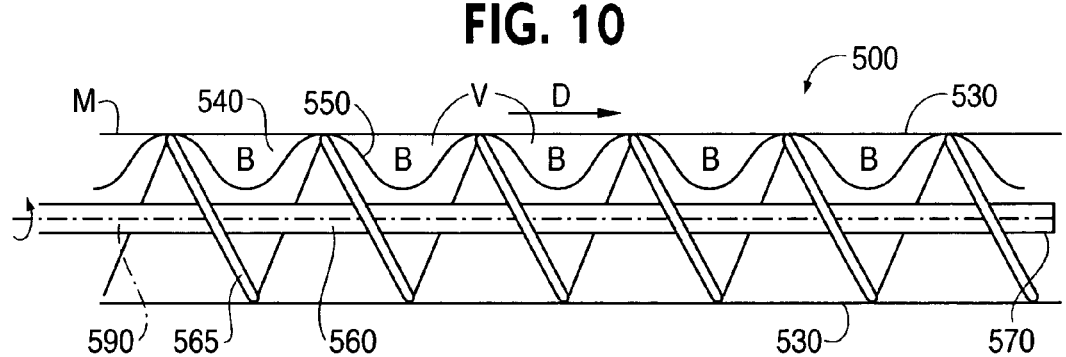

As shown in FIG. 10, catheter 10 has a lumen M defined by relatively rigid wall 530, an inner, elastic, fluid transport lumen 540, defined in part by wall 530 and in part by elastic inner lumen wall 550, and a screw drive system 560. Screw drive system 560 includes a helical thread 565 disposed about a central shaft 570, which is mounted for rotation about an axis 590.

Helical thread 565 engages elastic wall 550, and urges it toward wall 530, at numerous locations along lumen 540. Thread 565 thus narrows lumen 540 at those narrowing locations, defining between adjacent locations a fluid conveying volume V, which can contain a fluid bolus B. Rotation of shaft 570, and thus of helical thread 565, causes the narrowing locations, or points of impingement, to move distally along the lumen M in direction D. Boluses B of fluid are thereby transported along the length of the catheter 500 in the inner lumen 540.

In the embodiments disclosed above, the various displacement members are described as substantially narrowing the fluid delivery lumen. It should be understood that the narrowing of the lumen need only be sufficient to create more forward (distally directed) flow than back flow in the lumen, and need not fully close the lumen (especially in those embodiments with separate check valves).

Although the boluses of therapeutic material are preferably a liquid, several of the disclosed embodiments will also work to advance a bolus of solid therapeutic material.

In some embodiments above, the check valves are disclosed as opening in response to pressure. Alternatively, the valve or other mechanism by which movement of the therapeutic material between chambers of the lumen is controlled can be opened or closed and affected by other means, such as mechanically, electronically, or magnetically, such as in response to a control signal supplied by a control system.

While the invention has been described in detail and with reference to specific embodiments thereof, it will be apparent to one skilled in the art that various changes and modifications may be made therein without departing from the spirit and scope thereof. Thus, it is intended that the invention covers the modifications and variations of this invention provided they come within the scope of the appended claims and their equivalents.

What is claimed is:

1. A fluid delivery catheter, comprising:
   a catheter body;
   an elastic wall disposed within said catheter body and defining a lumen; and
   a peristaltic motion system disposed within said catheter body and operably engageable with said lumen to constrict said lumen at a plurality of axial positions along said lumen, wherein said peristaltic motion system includes a first rigid displacement cam and a second rigid displacement cam, the first rigid displacement cam distally displaced from the second rigid displacement cam, the first rigid displacement cam and the second rigid displacement cam each adapted for movement between a first cam position in which said rigid displacement cam constricts said lumen at one of said plurality of axial positions and a second cam position different than said first cam position.

2. A fluid delivery catheter, comprising:
   a lumen;
   a first balloon and a second balloon, each balloon being disposed within said lumen and selectively expandable to at least partially occlude said lumen, said second balloon distally offset from said first balloon;
   a partition disposed in said lumen between said first balloon and said second balloon, said partition dividing said lumen into a first lumen portion and a second lumen portion and fluidically isolating said first lumen portion from said second lumen portion; and a valve disposed in said partition and operable to selectively provide fluidic communication between said first lumen portion and said second lumen portion.

3. The catheter of claim 2, wherein said valve is a check valve operable to open in response to establishment of a predetermined pressure differential between said first lumen portion and said second lumen portion.

4. A fluid delivery catheter, comprising:

a catheter body;

a wall disposed in said catheter body and defining a lumen, said lumen having a proximal portion and a distal portion and said lumen being configured to contain and transport a liquid toward said distal portion;

a first rigid displacement cam member and a second rigid displacement cam member, the first rigid displacement cam member distally disposed from the second rigid displacement cam member, wherein the first rigid displacement cam member is adapted to selectively constrict said lumen at a first axial location along said lumen and the second rigid displacement cam member is adapted to selectively constrict said lumen at a second axial location along said lumen, the first rigid displacement cam member and the second rigid displacement cam member being configured to translate a volume distally along said lumen, whereby liquid contained in said volume is transported distally through said lumen;

a partition disposed in said lumen between said first axial location along said lumen and said second axial location along said lumen, said partition dividing said lumen into a first lumen portion and a second lumen portion; and a valve disposed in said partition and operable to selectively provide fluidic communication between said first lumen portion and said second lumen portion.

5. The catheter of claim 4, wherein said wall is elastic and said first rigid displacement cam member and said second rigid displacement cam member are substantially located external to said lumen and internal to said catheter body.

6. A fluid delivery catheter, comprising:

a catheter body;

an elastic wall disposed within said catheter body and defining a lumen;

a first balloon and a second balloon disposed within said catheter body, said first balloon and said second balloon being separate from and operably engageable with said elastic wall to constrict said lumen at a plurality of axial positions along said lumen, said first balloon distally displaced from said second balloon, and wherein said first balloon and said second balloon are each expandable from a first position at which said balloon constricts said lumen at one of said plurality of axial positions to a second position different from said first position;

a partition disposed in said lumen between at least two of said plurality of axial positions along said lumen, said partition dividing said lumen into a first lumen portion and a second lumen portion; and a valve disposed in said partition and operable to selectively provide fluidic communication between said first lumen portion and said second lumen portion.

7. A fluid delivery catheter, comprising:

a catheter body;

a wall disposed in said catheter body and defining a lumen, said lumen having a proximal portion and a distal portion and said lumen being configured to contain and transport a liquid toward said distal portion;

a first elastic, selectively extendable and collapsible member distally disposed from a second elastic, selectively extendable and collapsible member, each said elastic, selectively extendable and collapsible member being extendable independently from the other elastic, selectively extendable and collapsible member, the first elastic, selectively extendable and collapsible member when extended constricting said lumen at a first location along said lumen, the second elastic, selectively extendable and collapsible member when extended constricting said lumen at a second location along said lumen, the first elastic, selectively extendable and collapsible member and the second elastic, selectively extendable and collapsible member being configured to translate a volume distally along said lumen;

a partition disposed in said lumen between said first location along said lumen and said second location along said lumen, said partition dividing said lumen into a first lumen portion and a second lumen portion; and a valve disposed in said partition and operable to selectively provide fluidic communication between said first lumen portion and said second lumen portion.

8. The catheter of claim 7, wherein said first and said second elastic, selectively extendable and collapsible members are disposed substantially within said lumen.

9. The catheter of claim 7, wherein said first and said second elastic, selectively extendable and collapsible members are substantially located external to said lumen and internal to said catheter body.

* * * * *